(12) United States Patent
Misuchenko et al.

(10) Patent No.: US 8,662,745 B2
(45) Date of Patent: Mar. 4, 2014

(54) METHODS OF MEASURING CONDITIONS OF AN ULTRASONIC INSTRUMENT

(75) Inventors: Igoris Misuchenko, Saint-Petersburg (RU); Georgy Martsinovskiy, Saint-Petersburg (RU)

(73) Assignee: Covidien LP, Mansfield, MA (US)

( * ) Notice: Subject to any disclaimer, the term of this patent is extended or adjusted under 35 U.S.C. 154(b) by 67 days.

(21) Appl. No.: 13/294,743

(22) Filed: Nov. 11, 2011

(65) Prior Publication Data
US 2013/0121366 A1   May 16, 2013

(51) Int. Cl.
A61B 17/32   (2006.01)

(52) U.S. Cl.
USPC ............... 374/1; 606/169; 606/170; 606/171; 606/172; 606/173; 606/174

(58) Field of Classification Search
USPC .............................. 606/206, 169; 604/22, 169
See application file for complete search history.

(56) References Cited

U.S. PATENT DOCUMENTS

| | | | |
|---|---|---|---|
| 3,469,211 A | 9/1969 | Shoh et al. |
| 4,277,710 A | 7/1981 | Harwood et al. |
| 4,587,958 A | 5/1986 | Noguchi et al. |
| 4,827,911 A | 5/1989 | Broadwin et al. |
| 4,922,902 A | 5/1990 | Wuchinich et al. |
| 4,965,532 A | 10/1990 | Sakurai |
| 4,973,876 A | 11/1990 | Roberts |
| 4,974,581 A | 12/1990 | Wiksell |
| 5,180,363 A | 1/1993 | Idemoto et al. |
| 5,216,338 A | 6/1993 | Wilson |
| 5,330,502 A | 7/1994 | Hassler et al. |
| 5,421,829 A | 6/1995 | Olichney et al. |
| 5,456,684 A | 10/1995 | Schmidt et al. |
| 5,532,539 A | 7/1996 | Hielscher |
| 5,562,682 A | 10/1996 | Oberlin et al. |
| 5,634,466 A | 6/1997 | Gruner |
| 5,637,947 A | 6/1997 | Kising et al. |
| 5,649,957 A | 7/1997 | Levin |
| 5,700,952 A | 12/1997 | Andersen |
| 5,702,408 A | 12/1997 | Wales et al. |
| 5,704,534 A | 1/1998 | Huitema et al. |
| 5,707,369 A | 1/1998 | Vaitekunas et al. |
| 5,797,537 A | 8/1998 | Oberlin et al. |
| 5,816,476 A | 10/1998 | Buice et al. |
| 5,817,119 A | 10/1998 | Klieman et al. |
| 5,897,523 A | 4/1999 | Wright et al. |
| 6,063,098 A | 5/2000 | Houser et al. |

(Continued)

FOREIGN PATENT DOCUMENTS

| | | | |
|---|---|---|---|
| AU | 200179486 B2 | 5/2002 |
| CA | 2 359 403 A1 | 4/2002 |

(Continued)

*Primary Examiner* — Lisa Caputo
*Assistant Examiner* — Brandi N Hopkins

(57) ABSTRACT

A method of measuring conditions of an ultrasonic instrument includes providing an ultrasonic instrument that includes an end effector and a waveguide operably coupled to a generator and the end effector. The method involves generating one or more pulses with the generator, transmitting the one or more pulses to one or both of the waveguide and the end effector, generating one or more waves that scatter in an interferential pattern in response to the transmission of the one or more pulses, registering a signal indicative of the interferential pattern, generating an actual interferential pattern based upon the signal, and identifying one or more conditions of the end effector based upon the actual interferential pattern.

21 Claims, 7 Drawing Sheets

(56) References Cited

U.S. PATENT DOCUMENTS

| | | |
|---|---|---|
| 6,163,100 A | 12/2000 | Morizaki et al. |
| 6,241,139 B1 | 6/2001 | Milliman et al. |
| 6,320,298 B1 | 11/2001 | Kawabe |
| 6,454,782 B1 | 9/2002 | Schwemberger |
| 6,480,796 B2 | 11/2002 | Wiener |
| 6,569,109 B2 | 5/2003 | Sakurai et al. |
| 6,588,277 B2 | 7/2003 | Giordano et al. |
| 6,626,926 B2 | 9/2003 | Friedman et al. |
| 6,652,547 B2 | 11/2003 | Rabiner et al. |
| 6,663,641 B1 | 12/2003 | Kovac et al. |
| 6,666,854 B1 | 12/2003 | Lange |
| 6,678,621 B2 | 1/2004 | Wiener et al. |
| 6,679,899 B2 | 1/2004 | Wiener et al. |
| 6,752,815 B2 | 6/2004 | Beaupre |
| 6,761,690 B2 | 7/2004 | Sakurai et al. |
| 6,773,444 B2 | 8/2004 | Messerly |
| 6,898,536 B2 | 5/2005 | Wiener et al. |
| 6,984,919 B2 | 1/2006 | Iino et al. |
| 7,179,271 B2 | 2/2007 | Friedman et al. |
| 7,247,141 B2 | 7/2007 | Makin et al. |
| 7,270,646 B2 | 9/2007 | Sakurai et al. |
| 7,273,483 B2 | 9/2007 | Wiener et al. |
| 7,475,801 B2 | 1/2009 | Johansen et al. |
| 7,481,824 B2 | 1/2009 | Boudreaux et al. |
| 7,482,888 B1 | 1/2009 | Kleveland |
| 7,503,895 B2 | 3/2009 | Rabiner et al. |
| 7,513,160 B2 | 4/2009 | Lynch et al. |
| 7,514,844 B2 | 4/2009 | Unkrich |
| 7,528,670 B2 | 5/2009 | Soh |
| 7,566,334 B2 | 7/2009 | Christian et al. |
| 7,614,878 B2 | 11/2009 | Paschke et al. |
| 8,038,693 B2 * | 10/2011 | Allen ............................ 606/169 |
| 2002/0091404 A1 | 7/2002 | Beaupre |
| 2002/0128674 A1 | 9/2002 | Beaupre |
| 2003/0083683 A1 | 5/2003 | Schwemberger et al. |
| 2005/0027311 A1 | 2/2005 | Wiener et al. |
| 2005/0070800 A1 | 3/2005 | Takahashi |
| 2007/0112306 A1 | 5/2007 | Agnew |
| 2008/0234711 A1 | 9/2008 | Houser et al. |
| 2008/0277447 A1 | 11/2008 | Smith et al. |
| 2008/0294191 A1 | 11/2008 | Lee |
| 2008/0308607 A1 | 12/2008 | Timm et al. |
| 2009/0036913 A1 | 2/2009 | Wiener et al. |
| 2009/0036914 A1 | 2/2009 | Houser |
| 2009/0065549 A1 | 3/2009 | Viola |
| 2009/0069842 A1 | 3/2009 | Lee et al. |
| 2009/0076534 A1 | 3/2009 | Shelton, IV et al. |
| 2009/0105750 A1 * | 4/2009 | Price et al. .................... 606/206 |
| 2009/0118751 A1 | 5/2009 | Wiener et al. |
| 2009/0131962 A2 | 5/2009 | Houser et al. |
| 2009/0143797 A1 | 6/2009 | Smith et al. |
| 2009/0163836 A1 | 6/2009 | Sliwa |
| 2009/0187185 A1 | 7/2009 | Lyons et al. |
| 2009/0198272 A1 | 8/2009 | Kerver et al. |
| 2010/0087758 A1 | 4/2010 | Beaupre et al. |
| 2010/0204721 A1 | 8/2010 | Young et al. |
| 2011/0046522 A1 | 2/2011 | Chan et al. |

FOREIGN PATENT DOCUMENTS

| | | |
|---|---|---|
| EP | 0 908 155 | 4/1999 |
| EP | 1 199 046 B1 | 4/2002 |
| EP | 1 201 196 B1 | 3/2006 |
| EP | 2 000 106 A1 | 12/2008 |
| JP | 2000-237204 A | 9/2000 |
| WO | WO 02/062241 A1 | 8/2002 |

* cited by examiner

METHODS OF MEASURING CONDITIONS OF AN ULTRASONIC INSTRUMENT

BACKGROUND

1. Technical Field

The present disclosure relates to surgical instruments and, more particularly, to methods of measuring conditions of ultrasonic surgical instruments.

2. Background of Related Art

As an alternative to open instruments for use with open surgical procedures, many modern surgeons use endoscopes and endoscopic electrosurgical apparatuses (e.g., endoscopic or laparoscopic forceps) for remotely accessing organs through smaller, puncture-like incisions. These instruments are particularly suited for use in minimally invasive procedures, such as endoscopic or laparoscopic procedures where patients tend to benefit from less scarring, less pain, and reduced healing time. Typically, the endoscopic forceps is inserted into the patient through one or more various types of cannulas or access ports (typically having an opening that ranges from about five millimeters to about fifteen millimeters) that has been made with a trocar; as can be appreciated, smaller cannulas are usually preferred.

Some endoscopic instruments may utilize ultrasound vibrations to effectuate certain medical procedures. In particular, ultrasonic instruments utilize mechanical vibration energy transmitted at ultrasonic frequencies to treat tissue. When transmitted at suitable energy levels, ultrasonic vibrations may be used to coagulate, cauterize, fuse, cut, desiccate, and/or fulgurate tissue to effect hemostasis.

An endoscopic forceps that utilizes ultrasound and is configured for use with small cannulas (e.g., cannulas less than five millimeters) may present design challenges for a manufacturer of endoscopic instruments.

SUMMARY

According to one aspect, a method of measuring conditions of an ultrasonic instrument includes providing an ultrasonic instrument that includes an end effector and a waveguide operably coupled to a generator and the end effector. The waveguide may be curved. The method involves generating one or more pulses with the generator, transmitting the one or more pulses to one or both of the waveguide and the end effector, generating one or more waves that scatter in an interferential pattern in response to the transmission of the one or more pulses, registering a signal indicative of the interferential pattern, generating an actual interferential pattern based upon the signal, and identifying one or more conditions of the end effector based upon the actual interferential pattern.

The method may include providing the ultrasonic instrument with one or more sensors in electrical communication with the generator, registering the signal indicative of the interferential pattern with the sensor, and electrically communicating the signal from the sensor to the generator. The method may involve registering the signal for a predetermined time period, wherein the waveguide defines a predetermined length, wherein sound velocity in the waveguide is predetermined, and wherein the predetermined time period is greater than twice the predetermined length of the waveguide divided by the sound velocity in the waveguide. The method may involve sensing the signal with the generator and registering the signal with the generator.

One step may include positioning the end effector in contact with tissue, wherein the one or more conditions correspond to the interaction of the end effector and the tissue. The one or more conditions may include temperature, mechanical load, and/or relative positioning of the end effector. Each condition has one or more predetermined interferential patterns.

The method may involve adjusting the one or more pulses based upon the one or more conditions. The method may include adjusting the one or more pulses in response to differences between the actual interferential pattern and the one or more predetermined interferential patterns. The method may involve generating a series of pulses with the generator. The method may include providing a memory device operably coupled to the ultrasonic instrument, the memory device including one or more predetermined interferential patterns based upon the one or more conditions and comparing the actual interferential pattern with the one or more predetermined interferential patterns. The method may include calibrating an operating temperature range of the ultrasonic instrument from about room temperature to about three-hundred degrees centigrade.

One aspect of the present disclosure provides a method of measuring conditions of an ultrasonic instrument. The method includes the step of providing an ultrasonic instrument including a housing having a shaft extending therefrom, an end effector operably coupled to a distal end of the shaft, a waveguide operably associated with the shaft, and a transducer operably associated with the waveguide. The waveguide defines a predetermined length. Sound velocity in the waveguide is predetermined. The method involves generating one or more pulses with the transducer, transmitting the one or more pulses to the waveguide, registering one or more ultrasound waves reflected by one or both of the waveguide and the end effector in response to transmission of the one or more pulses, generating an interferential pattern of the one or more registered reflected ultrasound waves, and identifying one or more conditions of the end effector based upon the interferential pattern.

The method may involve the step of positioning the end effector in contact with tissue. The one or more conditions may correspond to the interaction of the end effector and tissue. The one or more conditions may include temperature, mechanical load, and/or positioning of the end effector relative to the shaft.

One step includes registering the one or more ultrasound waves for a predetermined time period that is greater than twice the predetermined length of the waveguide divided by the sound velocity in the waveguide.

The method may include the step of generating a series of pulses with the transducer. One step involves adjusting, the one or more pulses based upon the one or more conditions.

According to another aspect, the method includes providing a memory device operably coupled to the ultrasonic instrument. The memory device includes one or more predetermined interferential patterns based upon the one or more conditions. One step involves comparing the generated interferential pattern of the one or more registered reflected ultrasound waves with the one or more predetermined interferential patterns.

One step may involve calibrating the operating temperature range of the ultrasonic instrument from about room temperature to about three-hundred degrees centigrade.

BRIEF DESCRIPTION OF THE DRAWINGS

The above and other aspects and features of the present disclosure will become more apparent in light of the following detailed description when taken in conjunction with the accompanying drawings in which.

DETAILED DESCRIPTION OF THE EMBODIMENTS

Figure 1:
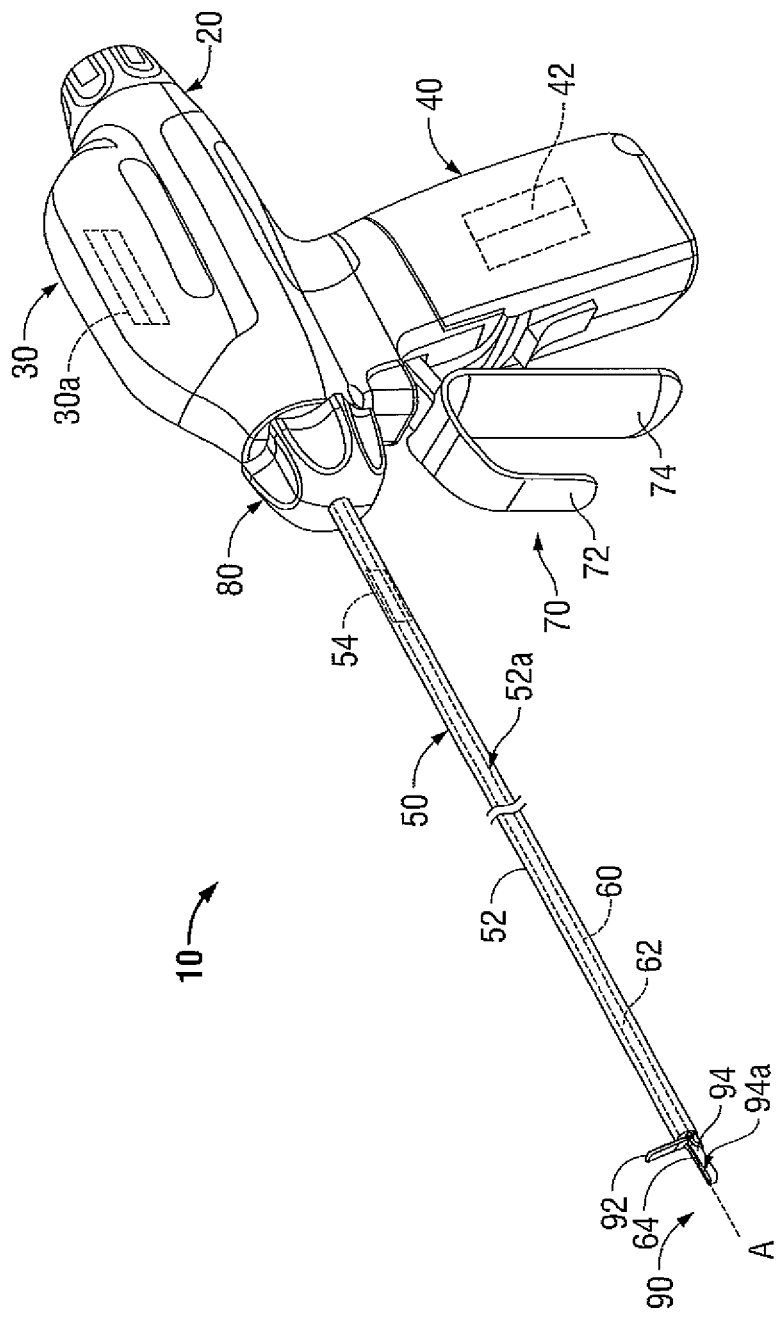
FIG. 1 shows a perspective view of one example of an ultrasonic instrument.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to an end which is closer to the user, while the term "distal" will refer to an end that is farther from the user.

With initial reference to FIG. 1, an embodiment of an ultrasonic instrument 10 (e.g., a forceps) is shown for use with various surgical procedures and generally includes a housing 20, a transducer assembly 30, an energy assembly 40, a shaft assembly 50, a waveguide assembly 60, a trigger assembly 70, a rotating assembly 80, and an end effector assembly 90 that mutually cooperate to grasp, seal, and divide tubular vessels and vascular tissue.

Figure 2:
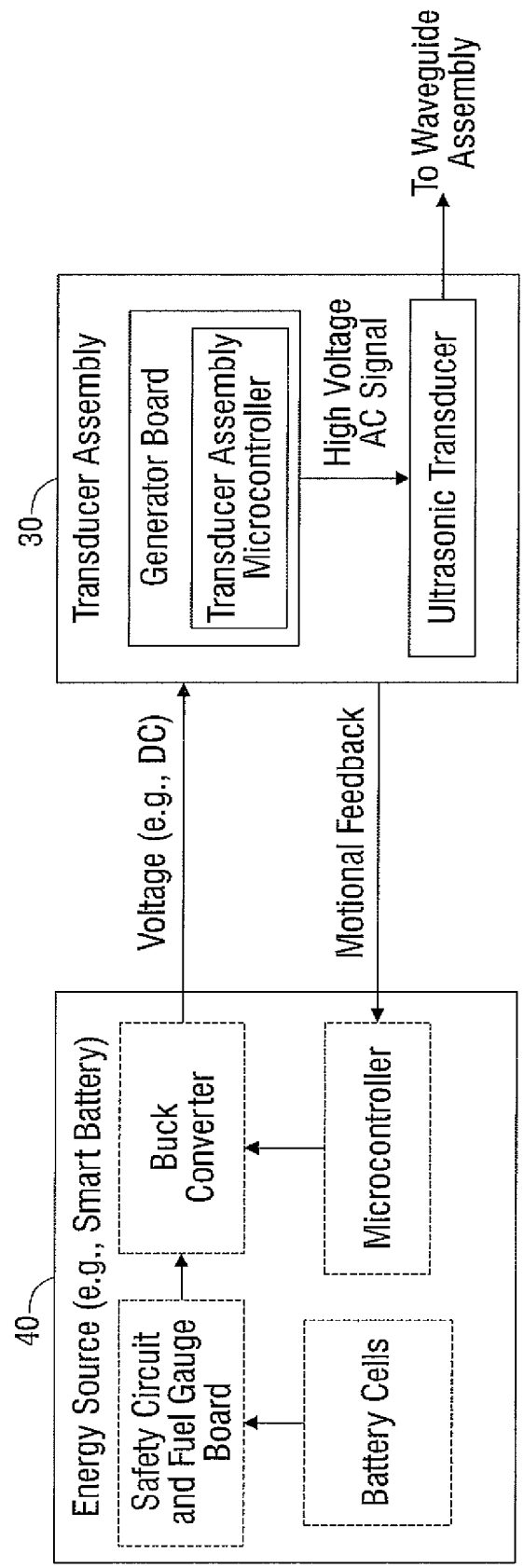
FIG. 2 is a block diagram depicting the interaction between an energy source and a transducer assembly of the ultrasonic instrument of FIG. 1.

Ultrasonic instrument 10 is powered by the energy assembly 40 when the energy assembly 40 is operably connected to the ultrasonic instrument 10. The energy assembly 40 may include one or more batteries 42 and/or one or more electrosurgical cables (not shown) to transfer energy, e.g. voltage from DC and/or AC signals, to the ultrasonic instrument 10. The ultrasonic instrument 10 may include a smart battery that controls the charge and discharge of its battery cells and communicates with the transducer assembly 30 as illustrated in FIG. 2.

In embodiments with one or more electrosurgical cables, the ultrasonic instrument 10 is connectable to an external source of electrosurgical energy, e.g., an electrosurgical generator (not shown). One such source of electrosurgical energy is described in commonly-owned U.S. Pat. No. 6,033,399 entitled "ELECTROSURGICAL GENERATOR WITH ADAPTIVE POWER CONTROL."

Figure 3:
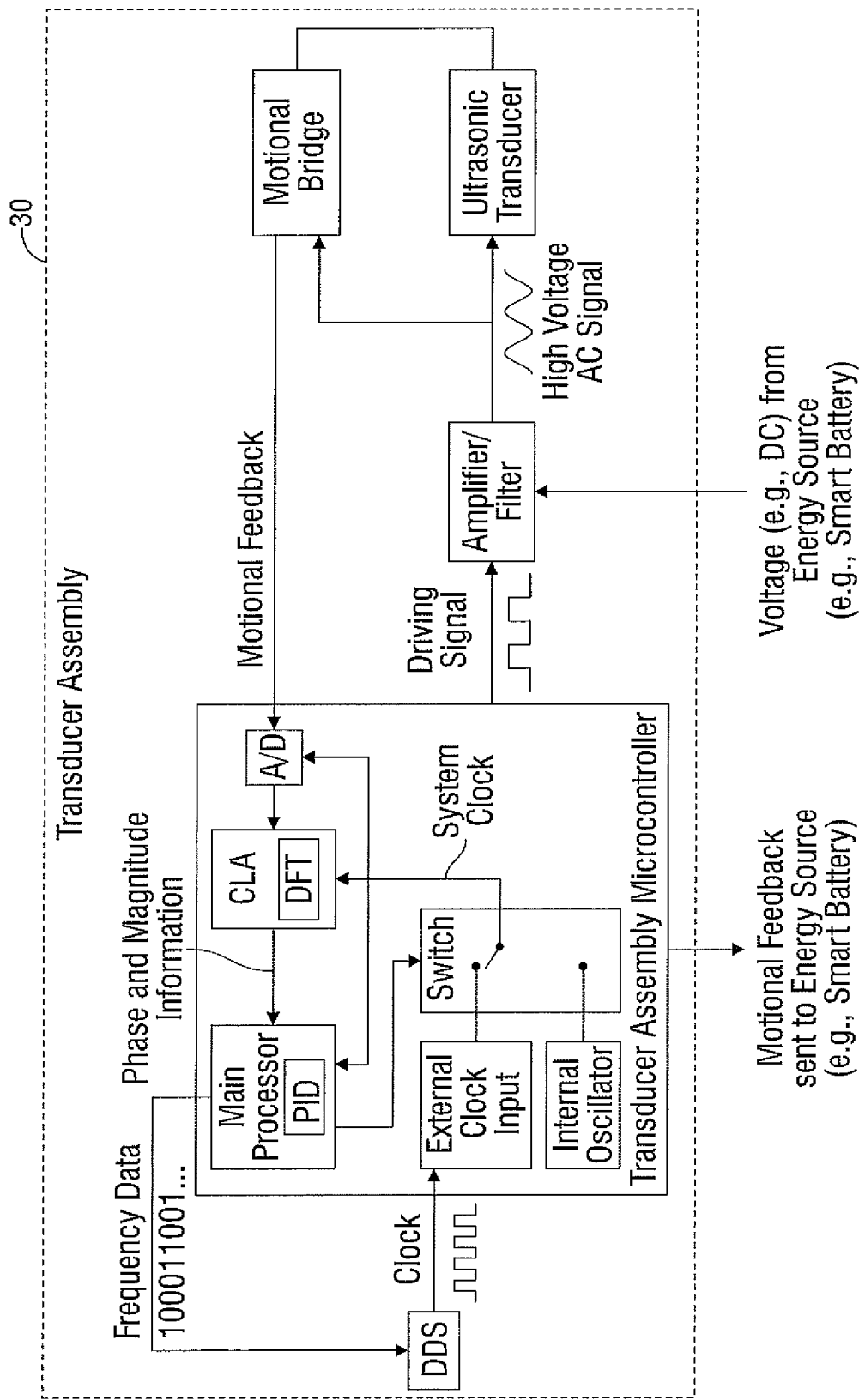
FIG. 3 is a block diagram depicting the transducer assembly of FIG. 2.

The transducer assembly 30 includes one or more ultrasonic transducers 30a operably coupled to the housing 20. Each transducer, which may be positioned within the housing 20, converts the energy transmitted thereto from the energy assembly 40 into high frequency mechanical motion, e.g., ultrasonic vibration. As such, the frequency of the ultrasonic vibration in the one or more transducers is controlled by the frequency of the energy signal, e.g., high voltage AC signal, applied to the one or more transducers. As depicted in FIG. 3, this frequency control may be accomplished by a phase-lock loop in the transducer assembly 30.

With reference to FIG. 1, the shaft assembly 50, which may be at least partially disposable, includes a shaft 52 which extends from the housing 20 and defines a central lumen 52a therethrough. The central lumen 52a receives at least a portion of the waveguide assembly 60 and a drive assembly 54 therein. The drive assembly 54 is operably coupled to the trigger assembly 70 at a proximal end of the drive assembly 54 and is operably coupled to the end effector assembly 90 at a distal end of the drive assembly 54 for operating the end effector assembly 90 upon the actuation of the trigger assembly 70.

The end effector assembly 90, which may be at least partially disposable, includes a pair of opposing jaw members 92, 94. The first jaw member 92 pivots relative to the second jaw member 94 via the drive assembly 54 upon the actuation of the trigger assembly 70, positioning jaw members 92, 94 between approximated (closed) and unapproximated (open) configurations. Second jaw member 94 defines a channel 94a therethrough.

With continued reference to FIG. 1, the waveguide assembly 60 is positioned within the shaft 52 of the shaft assembly 50 and is configured to receive and transmit the ultrasonic mechanical vibration generated by the one or more transducers. The waveguide assembly 60 includes a waveguide 62 and an ultrasonic treatment member 64 operably coupled to the distal end of the waveguide 62. The waveguide assembly 60 is at least partially positionable within one or both jaw members 92, 94 of the end effector assembly 90. More particularly, at least a portion of the ultrasonic treatment member 64 is positionable within the channel 94a defined by jaw member 94 of the end effector assembly 90. The ultrasonic treatment member 64 is configured to receive the mechanical vibration from the one or more transducers and transmit the mechanical vibration to treat tissue positioned within end effector assembly 90. The waveguide assembly 60 may be longitudinally translatable with respect to the end effector assembly 90.

The rotating assembly 80 is operatively connected to the housing 20 and is rotatable in either direction about the longitudinal axis of the shaft assembly 50 to rotate the shaft assembly 50 and the end effector assembly 90 about the longitudinal axis "A" of the shaft assembly 50. This enables the user to position and re-position the ultrasonic instrument 10 prior to activation and sealing. The rotating assembly 80 is operably coupled to the shaft assembly 50. A more detailed description of rotating assembly 80 is described in U.S. Pat. No. 7,101,371, entitled "VESSEL SEALER AND DIVIDER" by Dycus et al.

The trigger assembly 70 includes an activation trigger 72 for activating energy from the energy assembly 40 and a clamping trigger 74 for operating the end effector assembly 90. The trigger assembly 70 is operably coupled to the housing 20. The activation trigger 72 is configured to facilitate the transmission of the energy from the energy source 42 to the one or more transducers upon the actuation thereof. The clamping trigger 74 is configured to move the drive assembly 54 in order to move the opposing jaw members 92, 94 between unapproximated and approximated configurations upon the actuation of the clamping trigger 74. In this manner, the clamping trigger 74 of the trigger assembly 70 is operatively connected to the shaft assembly 50 to impart movement to first and second jaw members 92, 94 from an unapproximated (open) position, where the jaw members 92, 94 are in spaced relation relative to one another, to a clamping or approximated (closed) position, where the jaw members 92, 94 cooperate to grasp tissue therebetween.

In use, when the activation trigger 72 is actuated, the energy assembly 40 applies energy, e.g., the high voltage AC signal, to the transducer assembly 30. The activation trigger 72 may be configured to operate the ultrasonic instrument 10 in multiple modes of operation, including, but not limited to a low-power mode of operation and a high-power mode of operation. As discussed above, the energy is then converted by the transducer assembly 30 and transmitted from the transducer assembly 30 along the waveguide assembly 60 to the end effector assembly 90 in order to treat tissue grasped between the first and second jaws 92, 94 with ultrasonic vibrations.

Figure 4:
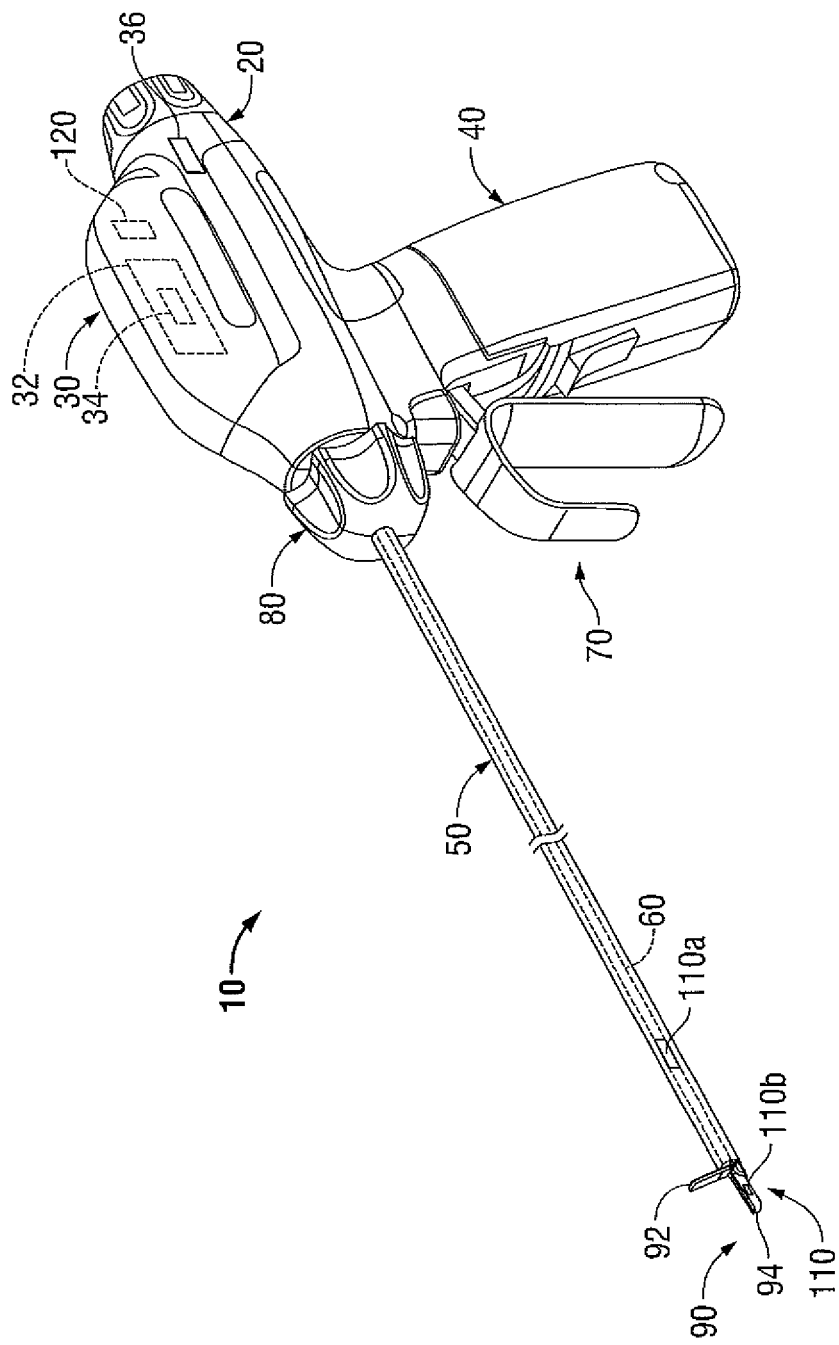
FIG. 4 shows a perspective view of one embodiment of an ultrasonic instrument in accordance with the principles of the present disclosure.

One embodiment of an ultrasonic instrument, generally referred to as 100, is depicted in FIG. 4. Ultrasonic instrument 100 is similar to ultrasonic instrument 10 and is described herein only to the extent necessary to describe the differences in construction and operation thereof. In particular, ultrasonic instrument 100 includes a housing 20 having a shaft assembly 50 extending therefrom, an end effector assembly 90 operably coupled to a distal end of the shaft assembly 50, a waveguide assembly 60 operably associated with the shaft assembly 50, and a transducer assembly 30 operably associated with the waveguide assembly 60. The waveguide assembly 60 defines a predetermined length and may be curved. Sound velocity in the waveguide assembly 60 may be predetermined.

Ultrasonic instrument 100 also includes one or more sensors 110 secured thereto that are electrically coupled to the transducer assembly 30 (e.g., via a generator 32 including a microcontroller 34 and/or any suitable electrical, mechanical, and/or electro-mechanical device(s) known in the art). With continued reference to FIG. 4, a first sensor 110a is shown positioned on the shaft assembly 50 and a second sensor 110b is shown positioned on jaw member 94 of end effector assembly 90. The sensors 110 may be positioned on any suitable portion of the ultrasonic instrument 100. The sensors 110 are configured to obtain data for enabling the generator 32 to determine one or more conditions of the ultrasonic instrument 100.

Figure 6:
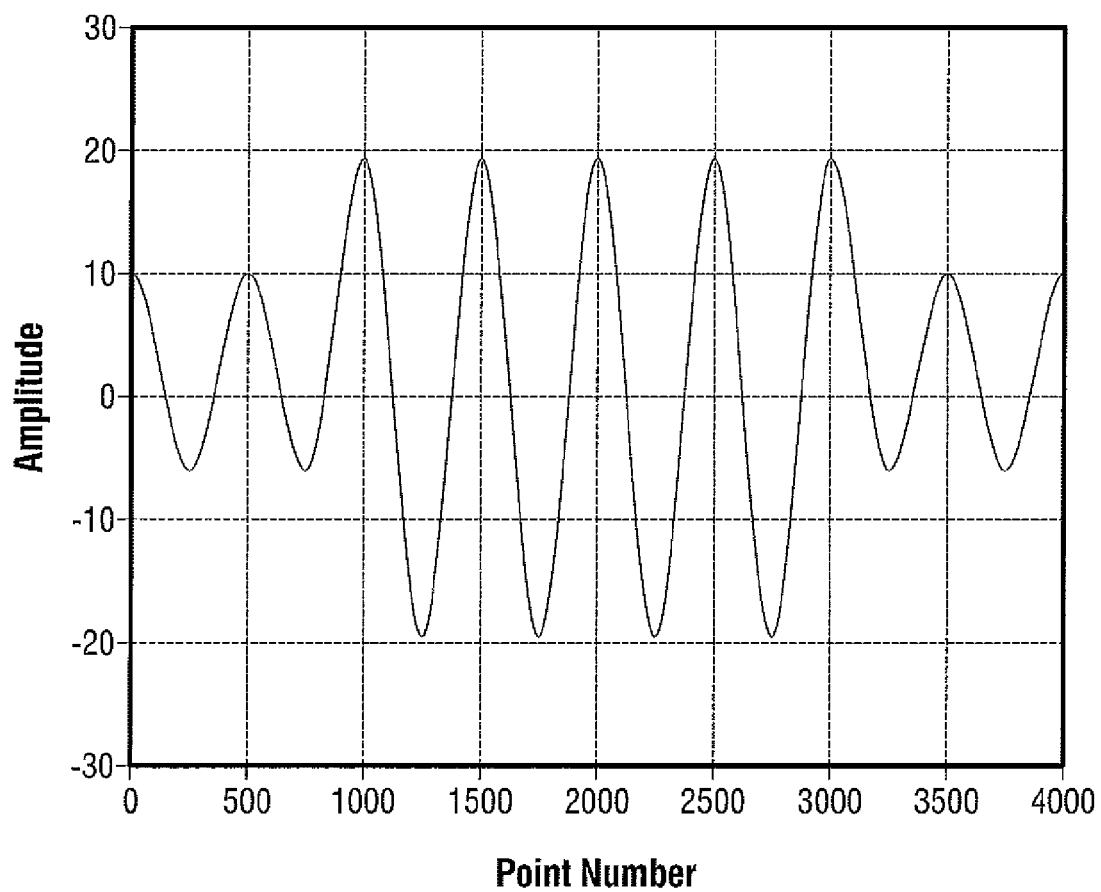
FIG. 6 shows a depiction of a predetermined interferential pattern in accordance with the present disclosure.
Figure 7:
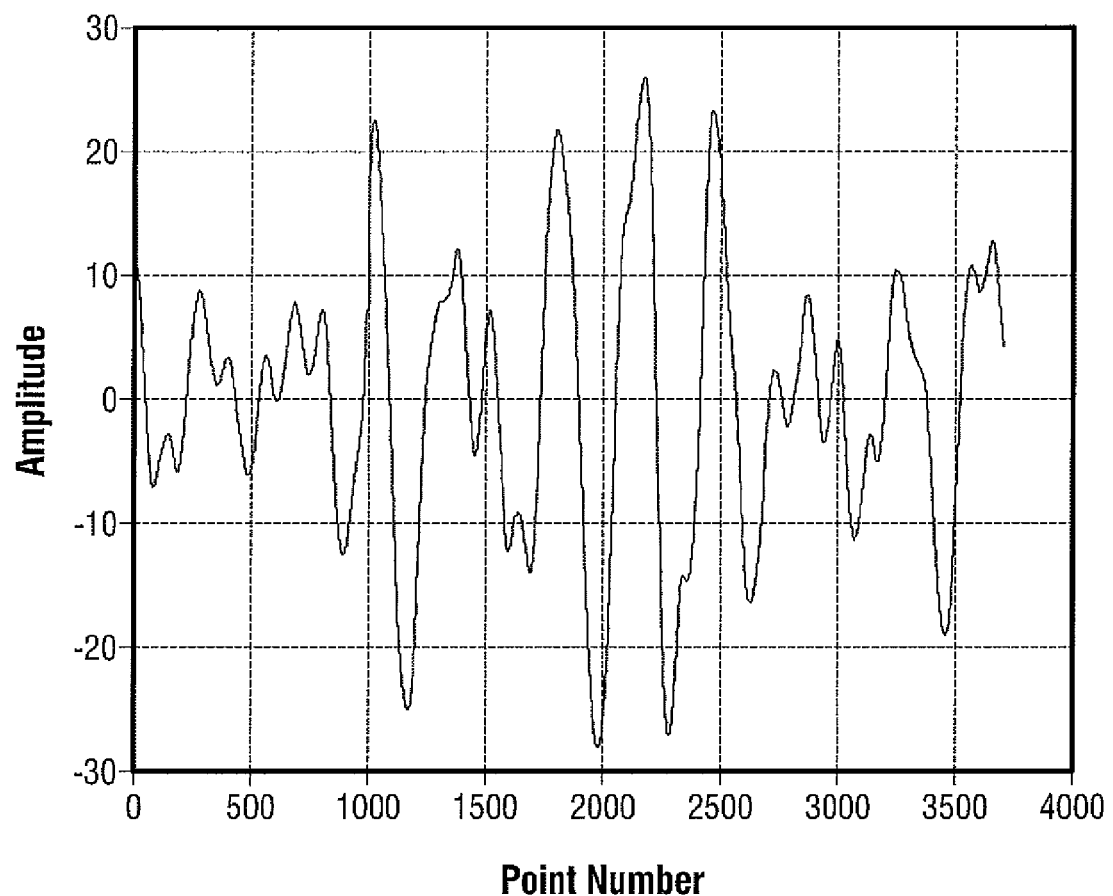
FIG. 7 shows a depiction of an actual interferential pattern produced by the presently disclosed ultrasonic instrument.

The ultrasonic instrument 100 may include an internal and/or external memory device 120. The memory device 120 may include one or more predetermined interferential patterns 200 (FIG. 6) based upon one or more conditions of the end effector assembly 90 and/or the waveguide assembly 60 (e.g., one or more of temperature, mechanical load, and positioning of the end effector assembly 90 relative to the shaft assembly 50) and/or may provide space to store data related to the one or more conditions (e.g., an actual interferential pattern 300 produced by the ultrasonic instrument as illustrated in FIG. 7). As such, this embodiment of the ultrasonic instrument 100 enables a user to measure various conditions of the ultrasonic instrument 100.

Figure 5:
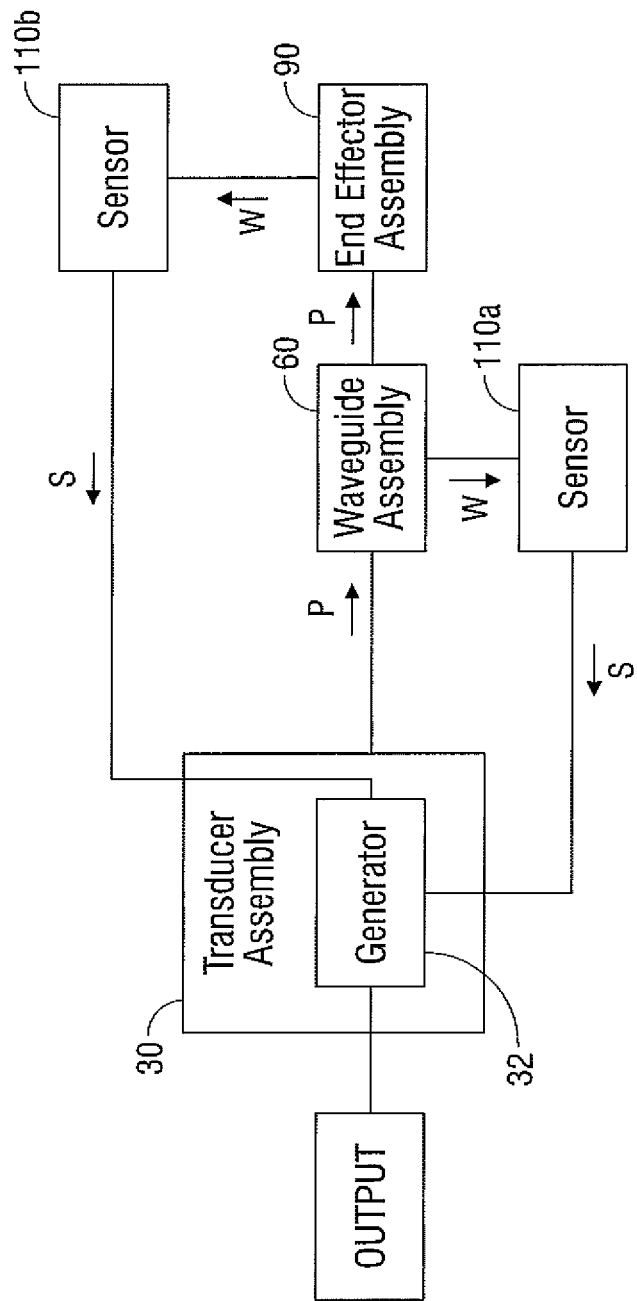
FIG. 5 is a block diagram depicting the operation of the presently disclosed ultrasonic instrument.

In operation, one or more pulses "P" are generated with the transducer assembly 30 (e.g., by virtue of the one or more transducers 30a; see FIG. 1) as depicted in FIG. 5. In embodiments, the generator 32 may be configured to generate and transmit the one or more pulses "P" or a series of pulses "P." The transducer 30 assembly may generate a series of pulses "P" with the one or more transducers 30a. The series of pulses "P" may have a frequency of at least about 200 cycles per nanosecond. The pulses "P" may be transmitted to the waveguide assembly 60 and the end effector assembly 90, for example, with a frequency of 5 MHz, a duration of 3 microseconds, and repetition rate of 4 kHz. However, any suitable frequency, duration, and repetition rate may be utilized. As the pulses "P" propagate or scatter through the waveguide assembly 60 and the end effector assembly 90, one or more waves "W", which may be ultrasonic waves, are reflected by one or both of the waveguide assembly 60 and the end effector assembly 90 in response to transmission of the one or more pulses "P." In this regard, the waveguide assembly 60 and/or the end effector assembly 90 may act collectively, or individually as a resonator to produce "echo" signals of the reflected waves "W."

To this end, pulse duration "t" may be selected to be noticeably shorter than double the length "L" of the resonator (e.g., one or both of the waveguide assembly 60 and end effector assembly 90) over the sound velocity V: $t=2L/V$. In this regard, the pulse repletion rate should be close to the resonant frequency (e.g., $V/2L$) of the resonator. The changes in the conditions in the end effector assembly 90 result in changes of the resonator properties. In particular, the changes make the resonant frequency deviate from its initial value. Variations of the resonator properties also result in shape changes in the actual interference pattern. For example, where temperature is a condition, then increasing temperature results in a slight change of the distance between scattering points of the propagated waves, resulting in a phase change of the propagated waves. The phase change is manifested by shape changes in the actual interference pattern when comparing the actual interference patterns of the lower and higher temperatures.

The sensors 110 collect data representative of the reflection of the one or more waves "W" and transmit the data via one or more signals "S" to the generator 32. In some embodiments, the generator 32 may also be used as a sensor to collect the data (e.g., by collecting the "echo" signal and converting the energy into an electrical signal). The generator 32 then registers (e.g., via microcontroller 34) the data transmitted via the one or more signals "S" and generates an interferential pattern of the one or more reflected waves "W." Based upon the interferential pattern produced, the generator (e.g., via the microcontroller 34) identifies the one or more conditions of the end effector assembly 90 and/or the waveguide assembly 60. The generator 32 may provide an output (e.g., via a display 36 operatively coupled to the ultrasonic instrument 100) of the one or more conditions. The output may be an audible, visual, or tactile signal of the one or more conditions. When the end effector assembly 90 is positioned in contact with tissue, the one or more conditions may correspond to the interaction of the end effector assembly 90 and tissue.

Further to the above, the one or more waves "W" may be registered for a predetermined time period (e.g., at least about 200 microseconds) that is greater than twice the predetermined length of the resonator (e.g., the waveguide assembly 60 and/or the end effector assembly 90), or portions thereof, divided by the sound velocity in the resonator.

Generated interferential patterns of the one or more registered reflected waves "W" may be compared (e.g., via the microcontroller 34) with the one or more predetermined interferential patterns stored on the memory device 120. The pulses "P" may be adjusted in response to differences between one or more generated interferential patterns and one or more predetermined interferential patterns. Each condition of the end effector assembly 90 and/or waveguide assembly 60 may have one or more predetermined interferential patterns.

In one mode of operation, the operating temperature range of the ultrasonic instrument 100 may be calibrated from about room temperature to about three-hundred degrees centigrade.

In use, the operator of one of the presently disclosed ultrasonic instruments 10, 100 receives information about conditions of the ultrasonic instrument, in real-time during operation thereof. For example, when the operator is aware of the temperature of the end effector assembly 90, the operator can avoid thermal damage of tissue being manipulated by the ultrasonic instrument.

With this purpose in mind, the presently disclosed ultrasonic instruments 10, 100 may include any suitable number of electrical connections, configurations, and/or components (e.g., resistors, capacitors, inductors, rheostats, etc.), mechanical connections, configurations, and/or components (e.g., gears, links, springs, members, etc.), and/or electromechanical connections, configurations, and/or components such that presently disclosed ultrasonic instrument 10, 100 may function as intended.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method of measuring conditions of an ultrasonic instrument comprising:
   storing a predetermined interferential pattern on a memory device;
   securing the memory device to an ultrasonic instrument including a generator, an end effector, and a waveguide that is coupled to the generator and the end effector;
   generating at least one pulse with the generator;
   transmitting the at least one pulse to at least one of the waveguide and the end effector;
   generating at least one wave that scatters in an interferential pattern in response to the transmission of the at least one pulse;
   registering a signal indicative of the interferential pattern;
   generating an actual interferential pattern based upon the signal;
   ascertaining differences between the actual interferential pattern and the predetermined interferential pattern by comparing the actual interferential pattern to the predetermined interferential pattern with the generator, the predetermined interferential pattern being established prior to a usage of the ultrasonic instrument; and
   identifying at least one condition of the end effector in real-time based upon the differences between the predetermined interferential pattern and the actual interferential pattern.

2. The method of claim 1, further including:
   registering the signal with at least one sensor in electrical communication with the generator; and
   electrically communicating the signal from the at least one sensor to the generator.

3. The method of claim 1, further including registering the signal for a predetermined time period, wherein the waveguide defines a predetermined length, wherein sound velocity in the waveguide is predetermined, and wherein the predetermined time period is greater than twice the predetermined length of the waveguide divided by the sound velocity in the waveguide.

4. The method of claim 1, further including positioning the end effector in contact with tissue, wherein the at least one condition corresponds to the interaction of the end effector and the tissue.

5. The method of claim 1, wherein the at least one condition includes at least one of temperature, mechanical load, and relative positioning of the end effector.

6. The method of claim 1, further including generating a series of pulses with the generator.

7. The method of claim 1, further including adjusting the at least one pulse based upon the at least one condition.

8. The method of claim 1, further including adjusting the at least one pulse in response to the differences between the actual interferential pattern and the predetermined interferential pattern.

9. The method of claim 1, wherein the at least one condition includes a plurality of conditions, each condition having at least one predetermined interferential pattern.

10. The method of claim 1, wherein transmitting the at least one pulse includes transmitting the at least one pulse to a curved waveguide.

11. The method of claim 1, further including calibrating an operating temperature range of the ultrasonic instrument from about room temperature to about three-hundred degrees centigrade.

12. The method of claim 1, further including:
    sensing the signal with the generator; and
    registering the signal with the generator.

13. A method of measuring conditions of an ultrasonic instrument comprising:
    storing at least one predetermined interferential pattern on a memory device;
    securing the memory device to an ultrasonic instrument, the ultrasonic instrument including a housing that supports a generator, a shaft that extends from the housing, a waveguide operably associated with the shaft, an end effector supported on a distal end of the shaft, and a transducer operably associated with the waveguide;
    generating at least one pulse with the transducer;
    transmitting the at least one pulse to the waveguide;
    registering at least one ultrasound wave reflected by at least one of the waveguide and the end effector in response to transmission of the at least one pulse;
    generating at least one actual interferential pattern of the at least one registered reflected ultrasound wave;
    ascertaining differences between the at least one actual interferential pattern and the at least one predetermined interferential pattern by comparing the at least one actual interferential pattern to the at least one predetermined interferential pattern with the generator, the at least one predetermined interferential pattern being established prior to a usage of the ultrasonic instrument; and
    identifying at least one condition of the end effector in real-time based upon the differences between the at least one predetermined interferential pattern and the at least one actual interferential pattern.

14. The method of claim 13, further including registering the at least one ultrasound wave for a predetermined time period, wherein the waveguide defines a predetermined length, wherein sound velocity in the waveguide is predetermined, and wherein the predetermined time period is greater than twice the predetermined length of the waveguide divided by the sound velocity in the waveguide.

15. The method of claim 13, further including positioning the end effector in contact with tissue, wherein the at least one condition corresponds to the interaction of the end effector and the tissue.

16. The method of claim 15, wherein the at least one condition includes at least one of temperature, mechanical load, and positioning of the end effector relative to the shaft.

17. The method of claim 13, further including generating a series of pulses with the transducer.

18. The method of claim 13, further including adjusting the at least one pulse based upon the at least one condition.

19. The method of claim 13, further including calibrating the operating temperature range of the ultrasonic instrument from about room temperature to about three-hundred degrees centigrade.

20. The method of claim 1, wherein comparing the actual interferential pattern to the predetermined interferential pattern with the generator is effectuated with a microcontroller of the generator.

21. The method of claim 13, wherein comparing the at least one actual interferential pattern to the at least one predetermined interferential pattern with the generator is effectuated with a microcontroller of the generator.

\* \* \* \* \*